United States Patent [19]

Gremmelmaier

[11] 4,141,919
[45] Feb. 27, 1979

[54] PROCESS FOR PRODUCING ALKOXY KETONES

[75] Inventor: Claude Gremmelmaier, Aesch, Switzerland

[73] Assignee: Ciba-Geigy Corporation, New York, N.Y.

[21] Appl. No.: 760,193

[22] Filed: Jan. 17, 1977

[51] Int. Cl.² .............................................. C07C 45/16
[52] U.S. Cl. .................................................... 260/594
[58] Field of Search .............................. 260/594, 590; 252/411 R

[56] References Cited

U.S. PATENT DOCUMENTS

| | | | |
|---|---|---|---|
| 1,999,388 | 4/1935 | Bader et al. ...................... | 252/411 R |
| 2,083,877 | 6/1937 | Steck et al. ........................... | 260/596 |
| 2,634,295 | 4/1953 | MacLean .............................. | 260/596 |
| 3,285,714 | 11/1966 | Poehler et al. ....................... | 260/596 |
| 3,462,495 | 8/1969 | Friedli .................................. | 260/594 |
| 3,554,930 | 1/1971 | Rogers et al. ......................... | 260/596 |

*Primary Examiner*—James O. Thomas, Jr.
*Assistant Examiner*—James H. Reamer
*Attorney, Agent, or Firm*—Karl F. Jorda

[57] ABSTRACT

A process for producing alkoxy ketones of formula I

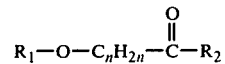

$$R_1-O-C_nH_{2n}-\overset{O}{\underset{\|}{C}}-R_2$$

wherein $R_1$ represents an alkyl group having 1 to 8 carbon atoms, $R_2$ represents hydrogen or an alkyl group having 1 to 4 carbon atoms, and n represents 1 or 2, by dehydrogenation of a corresponding alkoxyalkanol on a copper-containing catalyst which has been activated by treatment with hydrogen at 120° to 450° C., in which process the activated catalyst is firstly brought into contact at 230° to 350° C. with the vapor of the alkoxyalkanol to be dehydrogenated; hydrogen is subsequently passed over the catalyst at 250° to 450° C.; and then the dehydrogenation is performed at 150° to 450° C. on the catalyst pretreated in this manner, is disclosed.

8 Claims, No Drawings

PROCESS FOR PRODUCING ALKOXY KETONES

The present invention relates to a process for producing alkoxy ketones of the formula I

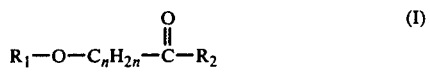

wherein
$R_1$ represents an alkyl group having 1 to 8 carbon atoms,
$R_2$ represents hydrogen or an alkyl group having 1 to 4 carbon atoms, and
$n$ represents 1 or 2,
by dehydrogenation of alkoxyalkanols of the formula II

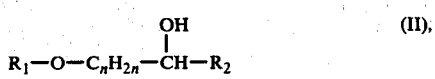

wherein $R_1$, $R_2$ and $n$ have the meanings given under formula I, on a copper-containing catalyst which, before dehydrogenation, has been activated by treatment with hydrogen at 120°–450° C.

Alkoxy ketones of the formula I are valuable intermediates in the production of N-substituted halogenoacetanilides having selective herbicidal action, such as are described, for example, in the German Offenlegungsschrift No. 2,328,340. Such N-substituted halogenoacetanilides are obtained by reductively alkylating an aniline alkylated in the nucleus with an alkoxy ketone of the formula I, and chloroacetylating the N-alkoxyalkyl aniline obtained.

It is known to activate before dehydrogenation copper-containing dehydrogenation catalysts by reduction. This reduction process can be either performed in an initial stage with the alcohol to be dehydrogenated or performed by means of a preliminary treatment with hydrogen at temperatures between 150° and 400° C. It has been shown that the catalysts obtained by reduction with hydrogen have a selectivity higher than that obtained in the case of reduction with the alcohol to be dehydrogenated. The improvement of the selectivity of the dehydrogenation catalyst obtainable by reduction with hydrogen is however still too low to obtain the desired alkoxy ketones of the formula I in the degree of purity required.

It is therefore the object of the present invention to provide a process for the production of alkoxy ketones of the formula I, by means of which process it is possible, by dehydrogenation of alkoxyalkanols of the formula II, to produce alkoxy ketones of the formula I with a selectivity higher than that obtained by processes hitherto known.

It has been found that alkoxyketones of the formula I are obtained with excellent selectivity on dehydrogenation of alkoxyalkanols of the formula II with the use of a copper-containing catalyst which has been activated by treatment with hydrogen at 150° to 400° C., by firstly bringing the activated catalyst at 230° to 350° C. in contact with the vapour of the alkoxyalkanol of the formula II to be dehydrogenated; passing hydrogen over the catalyst at 250° to 450° C.; and subsequently performing on the catalyst pretreated in this manner the dehydrogenation of the alkoxyalkanol of the formula II at 150° to 450° C.

Suitable copper-containing catalysts for performing the process according to the invention are, in particular, copper oxide or mixtures of copper oxide with other metal oxides, such as chromium oxide and zinc oxide. The catalysts can contain further additives such as alkaline-earth oxides and alkali oxides, e.g. barium oxide or sodium oxide. The catalysts can moreover be deposited on a carrier, such as silica gel.

The treatment, according to the invention, of the dehydrogenation catalyst with the alkoxyalkanol of the formula II to be dehydrogenated is performed as a rule during 0.5 to 2 hours. Longer treatment times are also possible, but offer no appreciable advantages. The duration of the treatment with hydrogen performed subsequently to the treatment with the alkoxyalkanol of the formula II to be dehydrogenated is as a rule 15 to 60 minutes. In this case too longer treatment times are possible, without however any further positive advantages being gained.

It is advantageous to perform the dehydrogenation of the alkoxyalkanols of the formula II at a temperature at most the same as that for the preceding treatment with hydrogen. Dehydrogenation is preferably performed at a temperature which is 10° to 30° C. lower than the temperature at which the preceding treatment with hydrogen has been carried out.

The treatment, according to the invention, of the dehydrogenation catalyst with the alcohol to be dehydrogenated is preferably performed at 250° to 350° C. The subsequent treatment of the dehydrogenation catalyst with hydrogen is carried out preferably at 250° to 350° C.

The process according to the invention is suitable in particular for the production of alkoxy ketones of the formula I wherein $R_1$ represents an alkyl group having 1 to 4 carbon atoms, $R_2$ represents hydrogen or methyl, and $n$ represents 1. For the dehydrogenation of the corresponding alkoxyalkanols of the formula II it has proved advantageous to use a copper-containing catalyst which has been activated at 140° to 320° C., to treat this at 250° to 300° C. with the vapour of the alkoxyalkanol of the formula II and subsequently at 250° to 320° C. with hydrogen, and to perform the dehydrogenation at 200° to 300° C.

It is also advantageous to carry out dehydrogenation in the presence of water. For this purpose, 1 to 15 percent by weight, preferably 3 to 10 percent by weight, of water is added to the alkoxyalkanol of the formula II to be dehydrogenated.

The process according to the invention is performed under normal pressure. The application of a slight vacuum or slight excess pressure is however likewise possible.

The catalysts pretreated according to the invention remain active as a rule for a long time. If necessary, however, the catalysts can be reactivated by reoxidation and subsequent pretreatment according to the invention.

It is possible by the process according to the invention to produce alkoxyketones of the formula I with excellent selectivity by dehydrogenation of alkoxyalkanols of the formula II. The enhancement of selectivity as a result of the pretreatment according to the invention is in no way theoretically explainable and must therefore be regarded as being surprising.

The process according to the invention is further illustrated by the following Examples.

EXAMPLE 1

Production of Methoxyacetone

A Pyrex-glass tube surrounded by a heating jacket and with an internal diameter of 30 mm, in which is incorporated a coaxial rod provided with thermocouples for measurement of the internal temperature, serves as the dehydrogenation reactor. The reactor is charged with 100 g of a dehydrogenation catalyst consisting of cylinders 3 mm in diameter and 3 mm in length and having the following composition:

| | |
|---|---|
| CuO | 78% |
| $Cr_2O_3$ | 20% |
| binder | 2% |

Above the catalyst packing is situated a preheating zone charged with inert fillers. Before the reactor is inserted an evaporator, into which can be introduced by means of a dosing pump the alcohol to be dehydrogenated.

Test A

The catalyst in the reactor is activated as follows:

1. A mixture of 1.3% by volume of hydrogen and 98.7% by volume of nitrogen (purity of the nitrogen = 99.99%) is passed at 150° C. for 15 hours over the catalyst with a spatial velocity of 3700 liters of gas per liter of catalyst and per hour.
2. Under otherwise the same conditions, a mixture of 5% by volume of hydrogen and 95% by volume of nitrogen is passed over the catalyst for 2 hours.
3. The temperature is raised at a heating-up rate of 50° to 70° C. per hour to 280° C. At this temperature, the catalyst is treated with a mixture of 5% by volume of hydrogen and 95% by volume of nitrogen for a further 3 hours, with retention of the aforementioned spatial velocity.

To effect dehydrogenation, 90 g per hour of methoxyisopropanol is passed over the catalyst at 250° C. The test results are summarised in Table I.

Test B 100 g of the catalyst used in Test A and activated in 3 stages as described therein is additionally activated by the following measures:

4. 100 ml per hour of methoxyisopropanol containing 5% by weight of water is evaporated, and the vapours are passed at 280° C. over the catalyst for 1 hour.
5. After a brief flushing of the reactor with nitrogen, pure hydrogen is passed for 30 minutes at 280° C. over the catalyst with a spatial velocity of about 300 liters per liter of catalyst and per hour.

To effect dehydrogenation, 90 g per hour of methoxyisopropanol containing 5% by weight of water is passed over the catalyst cooled to 250° C. in the nitrogen stream. The test results are summarised in Table I.

Table I

| Composition of product | Test A (comparison) | | Test B (process according to the invention) | |
|---|---|---|---|---|
| | after 20 h | after 60 h | after 20 h | after 60 h |
| methoxyacetone | 45.7 | 46.9 | 46.8 | 47.6 |
| methoxy-isopropanol | 38.1 | 38.8 | 41.6 | 42.5 |

Table I-continued

| Composition of product | Test A (comparison) | | Test B (process according to the invention) | |
|---|---|---|---|---|
| | after 20 h | after 60 h | after 20 h | after 60 h |
| acetone | 1.0 | 1.0 | 0.6 | 0.6 |
| secondary compounds except acetone | 9.8 | 8.2 | 5.7 | 4.2 |
| $H_2O$ | 5.4 | 5.0 | 5.4 | 5.0 |

From the results in Table I it is clear that as a result of the aftertreatment of the catalyst with hydrogen the formation of secondary products on subsequent dehydrogenation is reduced and hence selectivity can be improved. It is to be taken into account in this connection that the methoxyisopropanol used already contained 3.5% of secondary products.

EXAMPLE 2

The dehydrogenation reactor described in Example 1 is charged with 100 g of a mixed catalyst of the following composition:

| | |
|---|---|
| CuO | 32.05% |
| ZnO | 65.4% |
| NiO | 0.3% |
| FeO | 0.1% |
| CaO | 0.1% |

Test A

The catalyst is activated for 15 hours at 250° to 270° C. by passing over it a gas mixture consisting of 5% by volume of hydrogen and 95% by volume of nitrogen (spatial velocity = 2000 liters of gas mixture per 1 liter of catalyst and per hour). On the catalyst activated in this manner, there is then dehydrogenated at 300° C. 100 g/h of methoxyisopropanol containing 5% by weight of water. The composition of the resulting product after 20 and 60 hours can be seen from the following Table II.

Test B 100 g of the catalyst used in Test A is activated with hydrogen as described therein. 100 g/h of methoxyisopropanol containing 5% by weight of water is subsequently passed for 1 hour at 300° C. over the catalyst. The catalyst is afterwards treated for 30 minutes at 300° C. with pure hydrogen, with the spatial velocity being 400 liters of hydrogen per liter of catalyst and per hour. 100 g/h of methoxyisopropanol is then dehydrogenated at 300° C. on the catalyst activated in the said manner. The composition of the product obtained after 20 and 60 hours is given in the following Table II.

Table II

| Composition of product | Test A (comparison) | | Test B (process according to the invention) | |
|---|---|---|---|---|
| | after 20 h | after 60 h | after 20 h | after 60 h |
| methoxyacetone | 56.8 | 65.8 | 67.4 | 67.6 |
| methoxy-isopropanol | 20.0 | 18.8 | 20.4 | 21.4 |
| acetone | 7.2 | 3.9 | 2.7 | 1.6 |
| secondary compounds except acetone | 11.1 | 6.4 | 4.5 | 4.3 |
| $H_2O$ | 4.8 | 5.0 | 4.9 | 5.0 |

The test results show that the selectivity of the dehydrogenation is substantially improved by activation of the catalyst according to the invention. It is to be taken into account in this connection that the employed methoxyisopropanol already contained 3.5% of secondary compounds.

EXAMPLE 3

The dehydrogenation reactor described in Example 1 is charged with 100 g of the dehydrogenation catalyst used in Example 1. The activation of the catalyst is performed by the method given in Example 1. Methoxyisopropanol containing 5% by weight of water and 2.9% by weight of secondary products is then dehydrogenated to methoxyacetone on this catalyst in an extended time test. An accurate quantitative analysis is made in the period between 157 and 341 hours:

test period: 157-341 hours
throughput 8086 g of methoxyisopropanol
product obtained: 8108 g (including formed hydrogen).

Composition of the Product Obtained (Without Hydrogen)

| | |
|---|---|
| methoxyacetone | 41.85% |
| methoxyisopropanol | 49.6% |
| acetone | 0.27% |
| secondary products except acetone | 3.3% |
| water | 5.05% |
| gaseous secondary products | — |

From this product composition is calculated a conversion of 46.5% and a selectivity of 99.2%. It has been taken into account in this calculation that the employed methoxyisopropanol already contained 2.9% of secondary products.

EXAMPLE 4

100 g of the catalyst used in Example 1 is activated as follows:

1. A mixture of 1.3% volume of hydrogen and 98.7% by volume of nitrogen is passed at 150° C. for 15 hours over the catalyst with a spacial velocity of 3700 liters of gas per liter of catalyst and per hour.
2. Under otherwise identical conditions, a mixture of 5% by volume of hydrogen and 95% by volume of nitrogen is passed for 2 hours over the catalyst.
3. The temperature is raised at a heating-up rate of 50° to 70° C. per hour to 280° C. At this temperature, the catalyst is treated with a mixture of 5% by volume of hydrogen and 95% by volume of nitrogen for a further 3 hours, with retention of the aforementioned spatial velocity.
4. Vapours obtained by vaporisation of 100 ml per hour of methoxyisopropanol containing 5% by weight of water are passed at 280° C. for 1 hour over the catalyst. The composition of the resulting product is given in Table III.
5. After a brief rinsing of the reactor with nitrogen, pure hydrogen is passed over the catalyst for 30 minutes at 380° C. with a spatial velocity of about 300 liters per liter of catalyst and per hour.

90 g per hour of methoxyisopropanol containing 5% by weight of water and 3.5% by weight of secondary products is passed, for dehydrogenation, over the catalyst cooled to 250° C. in the nitrogen stream, and the composition of the product is continuously determined. The test results are summarised in Table III.

Table III

| Composition of product | Product from the 4th step of activation | Product after completion of activation (process according to the invention) | | |
|---|---|---|---|---|
| | | 0-8 hours | 8-16 hours | 16-24 hours |
| methoxyacetone | 45.7% | 46.4 | 47.1 | 46.8 |
| methoxyisopropanol | 23.3 | 40.3 | 41.1 | 41.6 |
| acetone | 4.8 | 0.8 | 0.6 | 0.6 |
| secondary compounds except acetone | 19.8 | 7.2 | 6.0 | 5.7 |
| H$_2$O | 6.6 | 5.3 | 5.2 | 5.4 |

The test results show that the drastic improvement of the selectivity attainable with activation according to the invention is present already immediately after completed activation.

What is claimed is:

1. A process for the production of an alkoxy ketone of the formula I $$R_1-O-C_nH_{2n}-\overset{O}{\underset{\|}{C}}-R_2 \qquad (I)$$

wherein
 $R_1$ represents an alkyl group having 1 to 8 carbon atoms,
 $R_2$ represents hydrogen or an alkyl group having 1 to 4 carbon atoms, and
 $n$ represents 1 or 2,
by dehydrogenation of an alkoxyalkanol of the formula II $$R_1O-C_nH_{2n}-\overset{OH}{\underset{|}{CH}}-R_2 \qquad (II)$$

wherein
 $R_1$, $R_2$ and $n$ have the meaning given above, on a copper-containing catalyst, which comprises the steps of:
 (a) treating the catalyst with hydrogen at a temperature of 120° to 450° C. for about 15 hours:
 (b) contacting the hydrogenated catalyst with the vapor of the alkoxyalkanol to be dehydrogenated at a temperature of 230° to 350° C. for 0.5 to 2 hours;
 (c) treating the catalyst again with hydrogen at a temperature of 250° to 450° C. for 0.25 to 1 hour; and
 (d) dehydrogenating the alkoxyalkanol of the formula at a temperature of 150° to 450° C.

2. A process for the activation of dehydrogenation catalysts containing copper oxide for use in the dehydrogenation of alkoxyalkanols of the formula $$R_1-O-C_nH_m-\overset{OH}{\underset{|}{CH}}-R_2$$

wherein
 $R_1$ represents an alkyl group having 1 to 8 carbon atoms,
 $R_2$ represents hydrogen or an alkyl group having 1 to 4 carbon atoms, and
 $n$ represents 1 or 2, to the corresponding carbonyl compounds, which comprises the steps of (a) treating the catalyst with hydrogen at a temperature of 120° to 450° C. for about 15 hours;
(b) contacting the hydrogenated catalyst with the vapor of the alkoxyalkanol to be dehydrogenated at a temperature of 230° to 350° C. for 0.5 to 2 hours; and
(c) treating the catalyst again with hydrogen at a temperature of 250° to 450° C. for 0.25 to 1 hour.

3. Process according to claim 1, wherein copper oxide or mixtures of copper oxide with other metal oxides are used as the copper-containing catalyst.

4. Process according to claim 1, wherein the treatment with the vapor of the alkoxyalkanol of the formula II to be dehydrogenated is performed at 250° to 350° C., the subsequent treatment with hydrogen at 250° to 350° C., and the dehydrogenation at 200° to 400° C.

5. Process according to claim 1, wherein the dehydrogenation of the alkoxyalkanol of the formula II is performed at a temperature at most the same as that for the preceding treatment with hydrogen.

6. Process according to claim 1, wherein the dehydrogenation of an alkoxyalkanol of the formula II is performed at a temperature which is 10° to 30° C. lower than the temperature at which the preceding treatment with hydrogen has been performed.

7. Process according to claim 1, wherein 1 to 15% by weight of water is added to the alkoxyalkanol of the formula II to be dehydrogenated.

8. Process according to claim 1, wherein the starting material is an alkoxyalkanol of the formula II wherein $R_1$ represents an alkyl group having 1 to 4 carbon atoms, $R_2$ represents hydrogen or methyl, and $n$ represents 1, in which process the dehydrogenation catalyst is firstly treated at 140° to 320° C. with hydrogen, subsequently at 250° to 300° C. with the vapour of the alkoxyalkanol to be dehydrogenated and then at 250° to 320° C. with hydrogen, and dehydrogenation is performed at 200° to 300° C.